(12) United States Patent  
Mangan

(10) Patent No.: US 6,307,362 B1
(45) Date of Patent: Oct. 23, 2001

(54) SOMATIC CELL ANALYSER

(75) Inventor: Steven L. Mangan, Gananoque (CA)

(73) Assignee: Agricultural Instruments Canada Ltd., Gananoque (CA)

(*) Notice: Subject to any disclaimer, the term of this patent is extended or adjusted under 35 U.S.C. 154(b) by 0 days.

(21) Appl. No.: 09/457,969

(22) Filed: Dec. 9, 1999

Related U.S. Application Data

(63) Continuation of application No. 09/024,569, filed on Feb. 17, 1998, now Pat. No. 6,031,367.

(51) Int. Cl.$^7$ .................................................. G01N 27/00
(52) U.S. Cl. .......................................... 324/71.4; 324/439
(58) Field of Search ........................... 324/71.4, 74, 439, 324/692

(56) References Cited

U.S. PATENT DOCUMENTS

| | | | |
|---|---|---|---|
| 3,762,371 | 10/1973 | Quayle et al. | 119/14.14 |
| 4,325,028 | 4/1982 | Takahashi | 324/442 |
| 4,385,590 | 5/1983 | Mortensen | 119/14.01 |
| 4,472,506 | 9/1984 | Liburdy | 324/71.4 |
| 4,771,007 | 9/1988 | Tippets et al. | 436/150 |
| 4,922,855 | 5/1990 | Tomizawa et al. | 119/14.15 |
| 5,302,903 | 4/1994 | De Jong et al. | 324/446 |
| 5,416,417 | 5/1995 | Peles | 324/439 |
| 5,771,837 | 6/1998 | Lely | 119/14.02 |

FOREIGN PATENT DOCUMENTS

| | | |
|---|---|---|
| 2059527 | 2/1992 | (CA). |
| 4134549 | 4/1993 | (DE). |
| 0211386 | 2/1987 | (EP). |
| 0397274 | 11/1990 | (EP). |
| 2123959 | 2/1984 | (GB). |

OTHER PUBLICATIONS

Lake, J.R. et al. "Trials of a Novel Mastitis Sensor on Experimentally Infected Cows", Journal of Dairy Research, vol. 59, pp. 11–19 (1992).

Nielen, M., et al., "Electrical Conductivity of Milk", J. Dairy Sci., vol. 75, pp. 606–614 (1992).

Linzell, J.L., et al., Day–to–Day Variations in Milk Composition in the Goat and Cow as a Guide to the detection of Subclinical Mastitis, British Veterinary Journal, vol. 128, pp. 284–294 (1972).

Siktberg, T.J., "Automatic Measurement of Milk Conductivity", Thesis, U. of Illinois, 1982.

Hamann, J., et al., Evaluation of the Electrical Conductivity of Milk as a Mastitis Indicator, Proposal to IDF–subgroup A2D (1996).

Primary Examiner—Safet Metjahic
Assistant Examiner—T. R. Sundaram
(74) Attorney, Agent, or Firm—Killworth, Gottman, Hagan & Schaeff, L.L.P.

(57) ABSTRACT

An on-line somatic cell analyser and a method for evaluating the quantity of somatic cells present in a sample of milk are provided. A flow cell is connected to a milking hose and admits a constant volume of sampled milk into a flow chamber. A probe with two electrodes is positioned in a zone of optimal sensing inside the flow chamber and provides a modulated signal with an intensity value corresponding to the number of sodium ions present in the sample. A detection unit receives the modulated signal and generates a ion count signal whenever the number of sodium ions is above a reference value. A control unit converts the ion count signal into a somatic cell count (SCC) score. A step graph comprising a plurality of SCC thresholds defining a plurality of milk categories is stored in a memory and used by the control unit to classify the sample in a quality category according to the SCC score of the sample. A set of parameters characterizing the respective milk quality category, including presence of either infectious or environmental mastitis, are finally displayed.

22 Claims, 8 Drawing Sheets

SOMATIC CELL ANALYSER

CROSS REFERENCES TO RELATED APPLICATIONS

This application is a continuation of U.S. patent application Ser. No. 09/024,569, filed Feb. 17, 1998, now U.S. Pat. No. 6,031,367, issued Feb. 29, 2000.

BACKGROUND OF THE INVENTION

1. Field of Invention

The present invention is generally concerned with milk quality analysis and in particular with an on-line, fully integrated somatic cell analyser.

2. Description of the Prior Art

The major cause of loss in dairy farming is an infection, known as mastitis, which occurs in an animal's udder. Mastitis is caused by contagious pathogens invading the udder and producing toxins that are harmful to the mammary glands. Generally, mastitis starts in one quarter.

Somatic cells, predominantly white cells and epithelial cells, enter the mammary gland as a result of damage to the alveolar lining by infection or chemical irritation. The counting of somatic cells excreted in the milk has become a widely used measure of mammary gland inflammation. The somatic cells can be counted by laborious direct microscopic method on stained milk smears, or the cell numbers can also be estimated by direct chemical tests. Other methods measure milk somatic cells indirectly or by determining the concentration of various by-products of the inflammatory response.

Somatic cell count (SCC), which is the number of white cells per millilitre of milk, increases in the bulk tank as mastitis spreads in the herd. SCC scores are used as an international standard in determining milk's quality and price. Most marketing organizations and regional authorities, regularly measure SCC on bulk tank milk and use these scores for penalty deductions and/or incentive payments. High SCC scores indicate the presence of mastitis in the herd and is reflected in the average score of the bulk tank. The bulk tank SCC is a good indicator of overall udder health and as good means for evaluating the mastitis control program.

It is also a high correlation between the bulk milk SCC and the average of individual animal counts. It is not uncommon for a few problem animals to be responsible for greater than 50% of the somatic cells in the bulk tank, particularly in small herds. It should be noted that animals with high milk production and intermediate SCC levels can have a significantly higher percentage of SCC contribution to the tank score than some high SCC cows with low production.

For high quality milk the SCC should be less than 200,000 cells/ml. Acceptable milk has SCC scores from 200,000 to 500,000 cells/ml. For infected animals, milk SCC scores are between 600,000 to 1.2M cells/ml.

When an animal in the herd becomes infected with infectious pathogens a rapid drop in milk production will be noted within 2 to 3 days. A high level of bacteria in an animal, causes an increased level of somatic cells in milk. An increased level of somatic cells in milk results in poorer quality milk products which are harder to process. About 80% of the losses attributed to a clinical episode involve the discarding of the nonsalable milk and decreased milk production. Additional losses are incurred by the farmer, such as premature culling and replacement heifer costs, or veterinary services and the cost for drugs. The loss is estimated to be US $184 per episode. In the USA alone, it is noted that over US$ 1 billion is lost in one year due to mastitis. The prevention procedures at milking are less efficient especially when the mastitis is in a subclinical phase and there are no visible signs of the disease. Special efforts have to be made at each milking to detect subclinical mastitis in individual animals before they become clinical episodes.

Milk production is also affected by the presence of environmental mastitis pathogens in animals. Generally, less than 10% of quarters in a herd are infected with environmental mastitis pathogens. Environmental mastitis causes a decrease in milk production but only to a mid level, where the SCC is between 350,000 to 500,000 cells/ml. Statistically, the risk factor for an animal with environmental mastitis pathogens to get infectious mastitis pathogens, is 60%.

Milk composition is influenced by many factors such as soil, feed, and water. It can also vary during milking, during the day, and with the season. The most frequent ions in milk are sodium and potassium ions which are transported passively from the secretory cells into the milk. Chloride ions are also found in milk but they have a higher concentration in the animal's blood and extracellular fluids than in milk. The concentration of potassium ions is relatively low in milk and the concentrations of sodium and chloride ions is relatively high.

Mastitis has a marked effect on milk composition. Generally, ion concentration in mastitic milk is higher than in normal milk. The electrical conductivity is higher in mastitic milk than in normal milk. In normal milk, electrical conductivity is about 3.1 miliSiemens/cm. A high electrical conductivity of milk of about 3.3 mS/cm indicates an infected quarter. The increase of electrical conductivity is due to an increase of sodium and chloride ion concentration.

Mastitis is currently detected by measuring changes in the electrical conductivity of milk. Electrical conductivity is generally measured with a DC or AC circuit having a probe positioned in the flow of milk. The most sensitive part of this on-line method is the probe. The probe generally includes two electrodes to which an AC or DC current is supplied to create an electrical circuit through the milk. The conductivity of the milk is evaluated by measuring the current variations in the circuitry that includes the probe. However, the readings are often inaccurate due to deposits of colloidal materials from the milk on the electrodes, and also due to polarization. Polarization occurs because some of the ions migrating towards the electrodes are not neutralized and consequently, an offset, or leakage current is generated between the electrodes. The presence of the leakage current results in inaccurate conductivity readings.

U.S. Pat. No. 3,762,371 issued to Joshua Creer Quayle et al. in 1973, describes an apparatus and a method for comparing the inductance of liquid streams for detecting mastitis. In this patent the suction teats engaging cup of a milking apparatus has a hemispherical chamber provided with four conductivity measuring cells. Each measuring cell includes a coil. The coils induce currents into the stream of milk from a quarter. The coils are placed in the arms of a four-arm electrical bridge which is balanced before testing. The induced currents change the impedance of the coil, depending on the electrical conductivity of the milk. An imbalance of the bridge during testing is due to variations in milk conductivity.

However, the system described in the above mentioned patent, is somehow complicated and not suitable for on-line measurements. Moreover, the system is based on the prediction that mastitis first occurs in one quarter, and can not detect mastitis occurring simultaneously in two or all quarters.

U.S. Pat. No. 5,416,417 issued to Eli Peles in 1995, discloses a method for determining the onset of mastitis by comparing the electrical conductivity of milk from an individual animal at milking with an average conductivity value previously recorded for the same animal. The average value corresponds to readings made during a predetermined period of time. A deviation between the measured electrical conductivity and the average value is determined at least once a day. Deviations of approximately 15% are considered an indication of the onset of mastitis.

This method does not provide an accurate indication about the type of mastitis or the degree of the infection.

U.S. Pat. No. 5,302,903 issued to Hendrik J. De Jong in 1994, describes a throughflow mastitis detector comprising two electrodes positioned at the bottom of a measuring chamber. The electrodes have a shank with a larger head projecting inside the measuring chamber, above and flush with the bottom surface, to avoid formation of areas where bacteria colonies may develop. This detector is not placed in an optimal sensing area. The milk flow is discontinued and obstructed by the measuring chamber. Moreover, milk fat/protein can build-up around electrodes causing current leakage. Also, cleaning the detector may be difficult.

Accordingly, there is a need for an improved on-line somatic cell analyser.

SUMMARY OF THE INVENTION

It is an object of the present invention to provide a milk analyser which alleviates totally or in part the drawbacks of the prior art.

It is another object of the present invention to provide an apparatus and a method for counting the somatic cells present in milk and to determine the quality of the milk in accordance with international standards.

It is a further object of the present invention to provide a device and a method for measuring a specific, reliable parameter in milk composition which gives an on-line, reliable SCC.

Still, another object of the present invention is to provide an accurate SCC indicator able to discriminate between a high SCC score recorded during the initial stage, for subclinical mastitis due to infectious pathogens, and same high SCC score recorded over a longer period of time, for clinical mastitis due to environmental pathogens.

According to one aspect of the invention, an on-line somatic cell analyser is provided. A flow cell having an inlet, an outlet, and a flow chamber is connected to the milking hose and admits a constant volume of liquid under test into the flow chamber. A probe with two electrodes is positioned within the flow chamber in a zone of optimal sensing and provides a modulated signal according to the number of sodium ions present in the sample. The analyser comprises detection means for providing an ion detection signal representing the number of sodium ions in the sample and for generating a ion count. Control means is also provided for receiving the ion count and for comparing same with a plurality of quality thresholds and for classifying the sample in a quality category. A set of parameters characterizing the respective quality category are finally displayed.

According to another aspect of the invention, a method for on-line measurement of the somatic cells present in milk is provided comprising the steps of inserting a flow cell in the flow of milk for providing a sample, measuring a ion detection signal representing the number of sodium ions in the sample, measuring a ion count based on the ion detection signal, converting the ion count into real time SCC, and comparing said real time SCC with a plurality of SCC thresholds for classifying the milk in a quality category.

The present invention provides for an on-line somatic cell analyser easy to use by a farmer, displaying SCC scores which are the international standards for evaluating the quality of the milk. The device of the present invention can be manufactured at a low cost.

BRIEF DESCRIPTION OF THE DRAWINGS

The present invention will be better understood from the following description with reference to the drawings where.

DETAILED DESCRIPTION OF THE PREFERRED EMBODIMENT

Milk has electrolytic properties. The number of sodium ions in milk chemistry appears to be the most reliable indicator of mastitis. Firstly, the number of sodium ions is higher compared to the number of any other ions present in milk and therefore, sodium ions can be counted with more accuracy. Secondly, the number of sodium ions is unaffected by other factors impacting on the conductivity of milk, but the somatic cells. Further on, the variations in the conductivity of milk can give, with proper calibration, the variations in the number of somatic cells present in milk. Based on this direct dependency, the present invention measures the conductivity of a constant volume of milk and displays a SCC score.

General and special tests were designed for testing selected samples of milk with and without sodium ions. The results of more than 2,000 milkings were used for calibrating the somatic cell analyser of the present invention, by transforming the milk conductivity variations into a number of sodium ion detections, and then correlating a somatic cell count to the number of sodium ion detections.

Based on experimental work and laboratory testing, a method and a somatic cell analyser have been developed for counting the sodium ions present in milk, the analyser being calibrated to display directly the number of somatic cells/ml of milk, according to the number of sodium ions detected.

Case 1: Infectious Mastitis

Figure 1A:
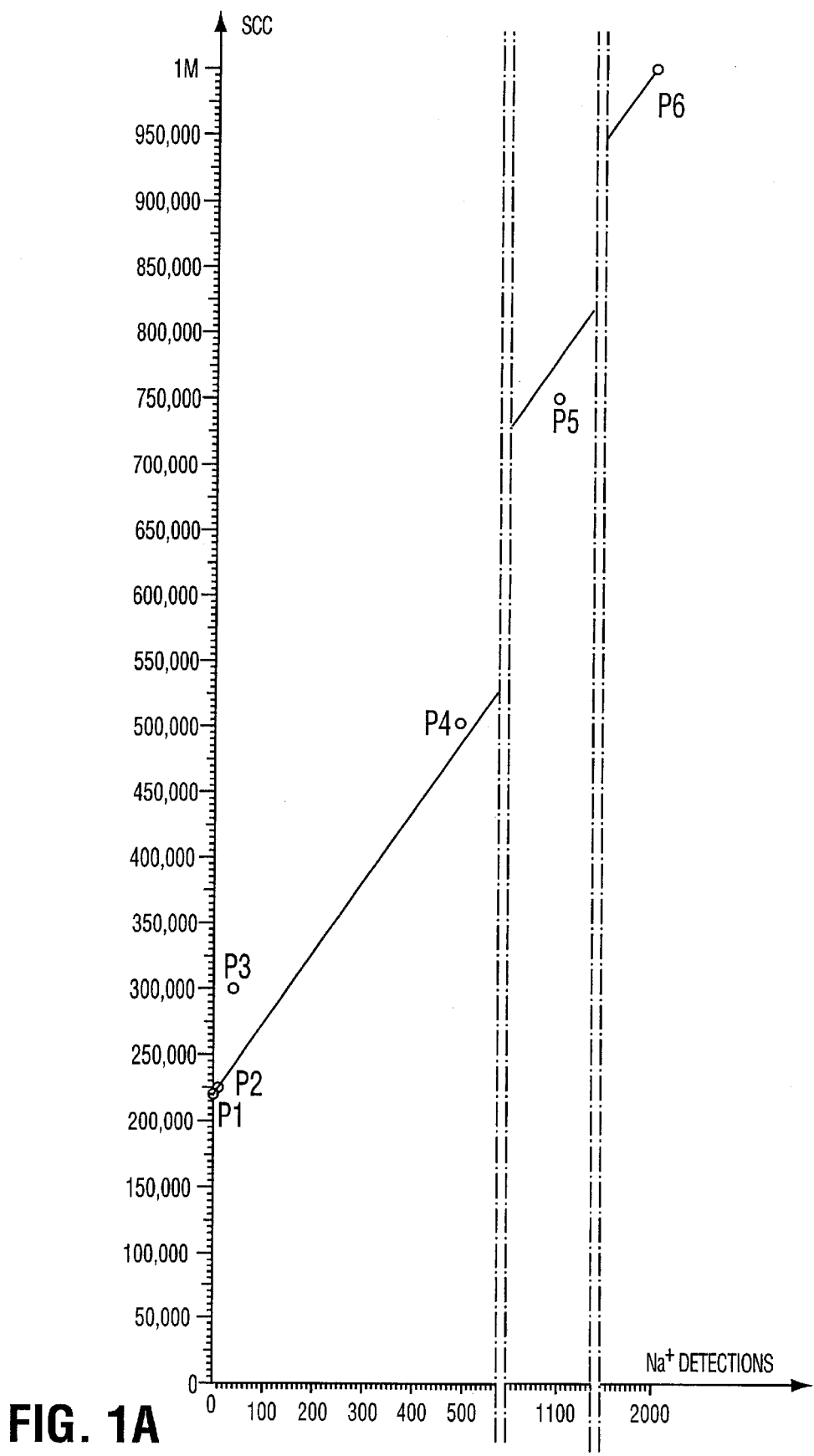
FIG. 1A is a graph plotting SCC against sodium ion detections in the case of infectious mastitis.

FIG. 1A is an experimental graph illustrating the relationship between the number of sodium ions detected in milk, shown on the abscissa, and the SCC scores, shown on the ordinate. The graph includes results from animals which developed infectious mastitis, and the data were sampled over a one week interval. The word "animal" designates here any milk producing animal.

The graph shows that an increase of sodium ions in milk is in direct relation to a rapid increase in the number of somatic cells, which is characteristic of infectious mastitis present in an animal. Line $p_1$–$p_6$ interpolates the experimental results shown in discrete points $p_1$–$p_6$. This graph shows how the infectious mastitis develops, generally in less than 1 week.

Infectious mastitis causes an increase in the number of the sodium ions and a corresponding increase in the number of the somatic cells in milk. The increase in somatic cells is combined with a substantial decrease in milk production. As such, whenever the SCC reaches the level of +400,000 cells/ml in a short period of time, the animal must be isolated and treatment with antibiotics is required.

Case 2: Environmental Mastitis

Environmental mastitis develops in a period of time between 10 days to 4 months. The experiments show that in the case of environmental mastitis, the increase in density of sodium ions in milk is less dramatic compared to infectious cases. The SCC is practically constant at +300,000 cells/ml for a long period of time. This is partially due to the fact that the milk production does not decrease as much as in infectious cases.

Figure 1B:
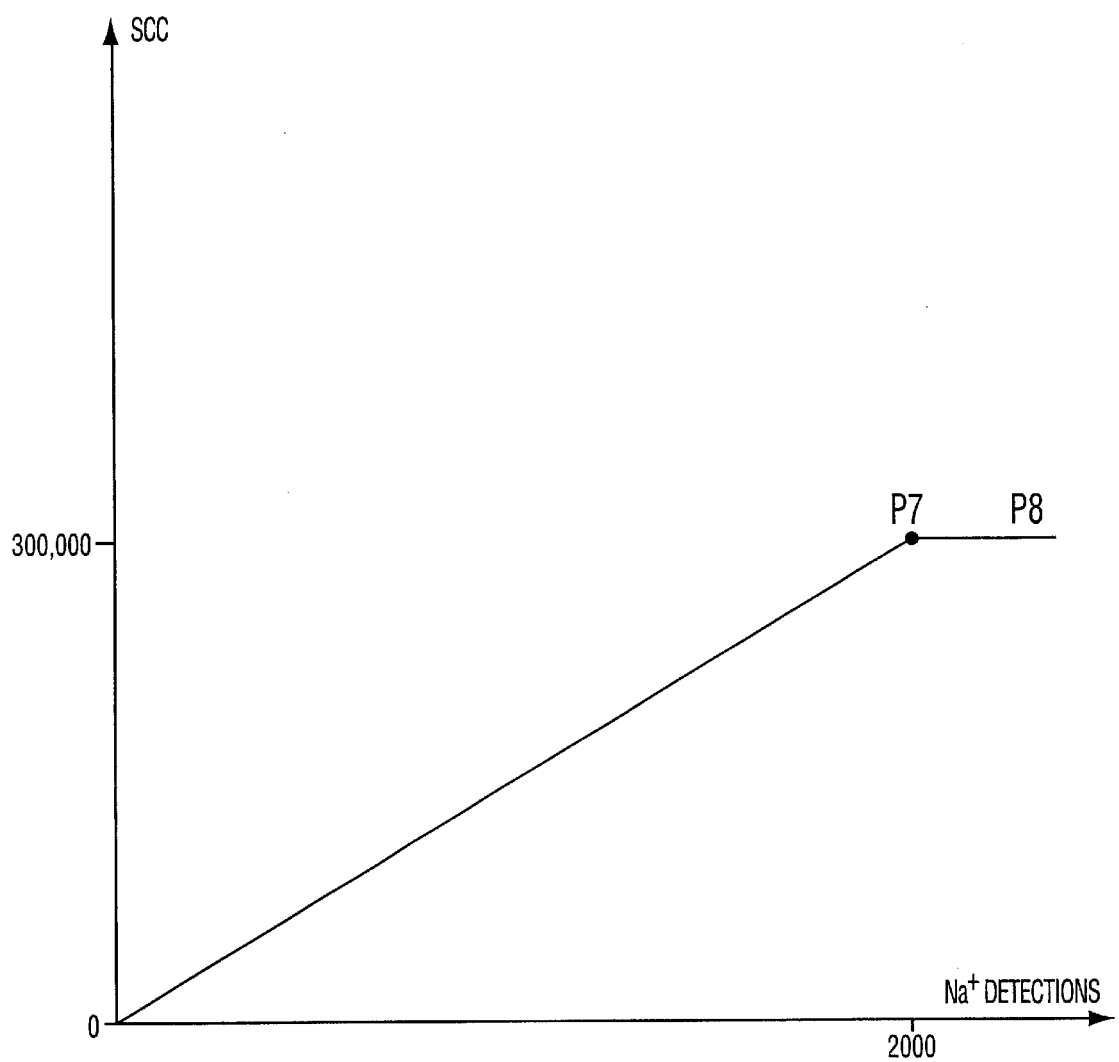
FIG. 1B is a graph plotting SCC against sodium ion detections in the case of environmental mastitis.
Figure 1C:
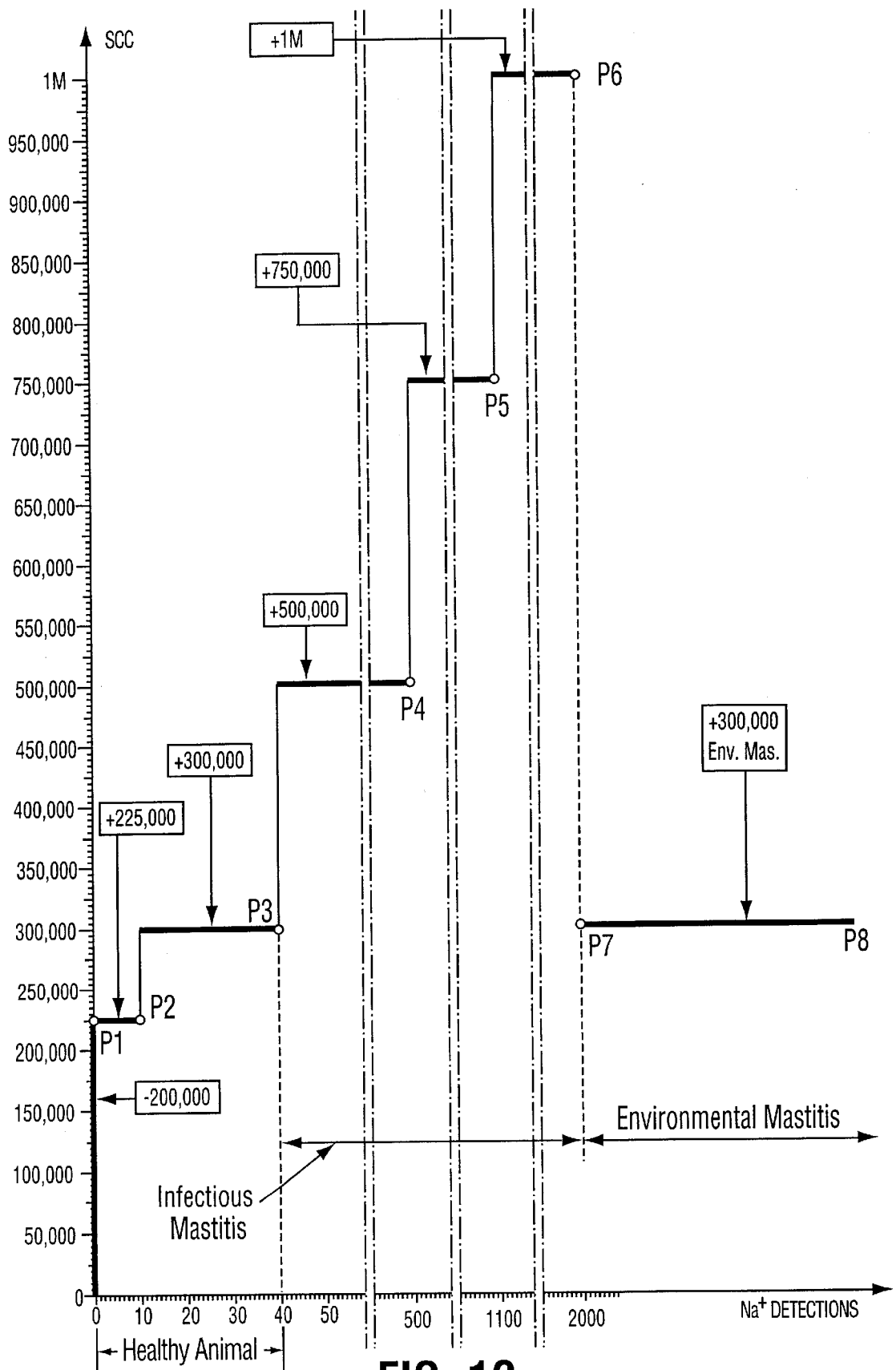
FIG. 1C is a SCC—sodium ion detections calibration graph used by the somatic cell analyser of the present invention.

As shown in FIG. 1B, sodium ion detections are in excess of 2,000 in section $p_7$–$p_8$ of the graph, but the SCC is low, shown on FIGS. 1A and 1C. A SCC score of −200,000 cells/ml displayed for point p, indicates the absence of sodium ions in milk and a very low number of somatic cells in milk. Such milk would qualify for a premium.

"+225,000 cells/ml" denotes an animal having over 200,000 cells/ml and corresponds to point $P_2$ shown on FIGS. 1A and 1C. This animal should be closely observed and supervised.

"+300,000 cells/ml" corresponds to points $p_3$, shown on FIGS. 1A and 1C, and $p_7$, shown on FIGS. 1B and 1C. Such a score can be associated with either infectious or environmental mastitis, depending on the number of sodium ion detected and taking also into account the length of time for the animal to reach and maintain this SCC.

"+500,000 cells/ml" is the Canadian somatic cell rejection level and corresponds to point $p_4$ shown on FIGS. 1A and 1C. This milk must be discarded.

"+750,000 cells/ml is the USA somatic cell rejection level and corresponds to point $p_5$ shown on FIGS. 1A and 1C.

"+1,000,000 cells/ml" is used more for laboratory testing and corresponds to point $p_6$ shown on FIGS. 1A and 1C. At this level of the infection the composition of the milk is visibly altered.

Six thresholds of sodium ion detections corresponding to the above identified SCC scores have been experimentally determined. The thresholds of sodium ion detections are: 0; 10; 40; 500; 1,100; and 2,000, respectively.

An additional SCC score "+300,000 cells/ml ENV MAS", section $p_7$–$p_8$ of FIGS. 1B and 1C, is identified with environmental mastitis. A SCC score of +300,000 cells/ml associated with a number of sodium ions detections in excess of 2,000, is relevant for animals with clinical environmental mastitis.

The seven SCC and the related thresholds are shown in Table 1 for easy reference.

TABLE 1

| Graph | Section | $p_1$–$p_2$ | $p_2$–$p_3$ | $p_3$–$p_4$ | $p_4$–$p_5$ | $p_5$–$p_6$ | $p_7$–$p_8$ |
|---|---|---|---|---|---|---|---|
| Detected | 0 | 0 → 10 | 11 → 40 | 41 → 500 | 501 → 1100 | 1101 → 2000 | ≧2001 |
| SCC | −200000 | +225000 | +300000 | +500000 | +750000 | +1M | +300000 EnvMas | under the level of 400,000 cells/ml. Irrespective of the small SCC scores, when an animal presents over 2,000 sodium ion detections for a longer period of time, it requires special attention to determine the cause of the high sodium ion count. It can be caused by poor pond water, a foot infection, pneumonia, or E-coli bacteria which spread generally on hot summer days. In such a case, the sodium ion count will decrease by improving the sanitary conditions only, without using antibiotics.

Calibration Protocol

In practice, a precise measurement of the SCC scores is not critical. Therefore, the present invention proposes to use various levels of meaningful SCC scores, as shown in the step graph of FIG. 1C. The two distinct sections $p_1$–$p_6$ and $p_7$–$p_8$ of the graph of FIG. 1C help identify when an animal is infected with mastitis, how severe the infection is, and what type of pathogens intruded into the udder.

The graph of FIG. 1C also illustrates how the somatic cell analyser is calibrated. Each SCC score is characteristic of a quality of milk. The seven SCC scores displayed by the analyser were selected for the reasons set out below:

"−200,000 cells/ml" denotes an uninfected animal with less than 200,000 cells/ml and corresponds to point $p_1$ The following is a description of the preferred embodiment of the invention.

Figure 2:
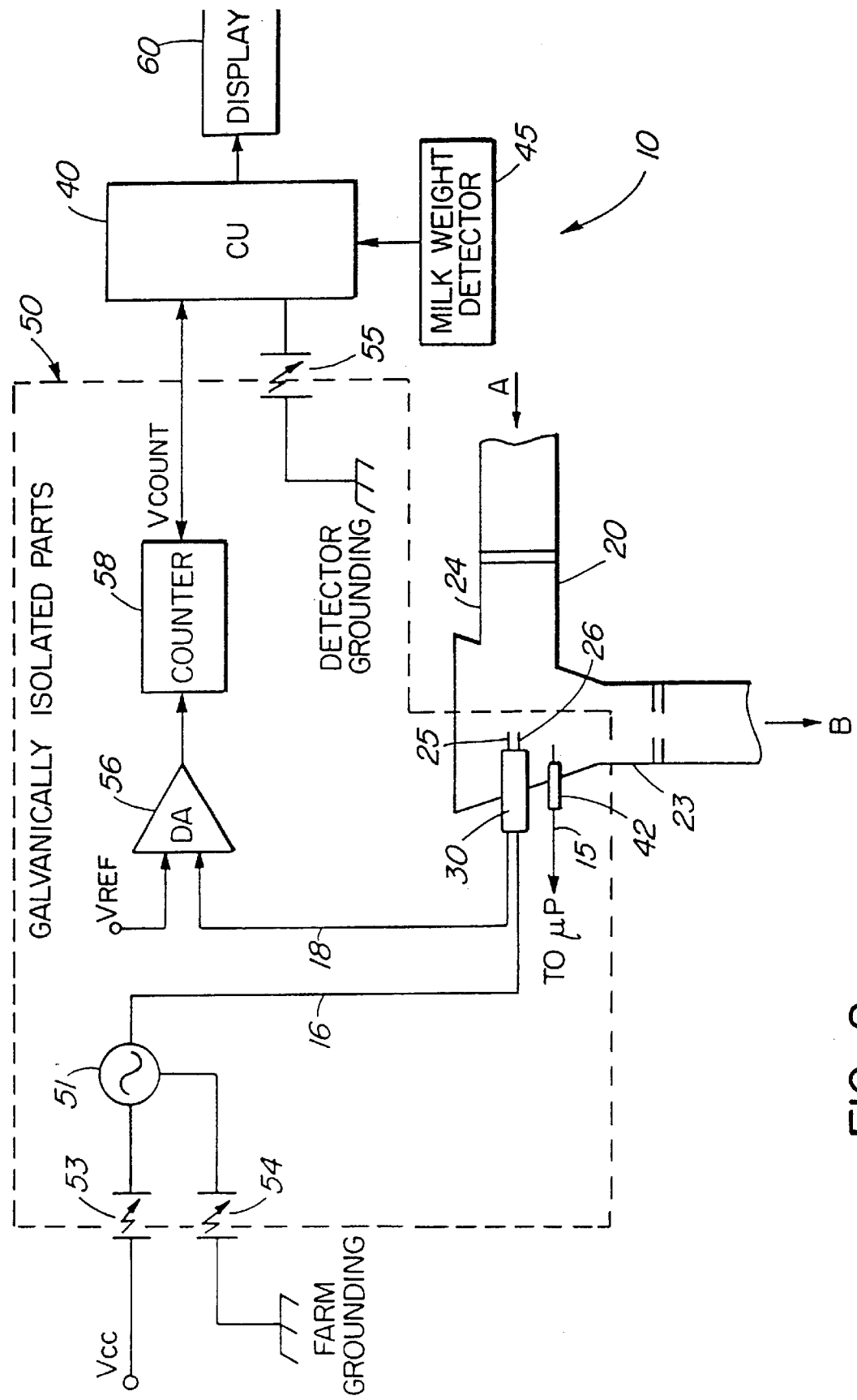
FIG. 2 is a block diagram of the somatic cell analyser of the present invention.

FIG. 2 is a block diagram of an on-line, fully integrated somatic cell analyser 10 of the present invention. Device 10 comprises a power supply (not shown), a control unit 40, a sodium ion detector 50, and a display 60. FIG. 2 also shows a flow cell 20 connected to the milk circuit for continuously sampling the milk, as it will be detailed in connection with FIGS. 3A, 3B, 4, and 5.

The sodium ion detector 50 comprises a probe 30 which is embedded in a plastic support and placed inside flow cell 20. Probe 30 has two electrodes 25 and 26, in direct contact with the milk, and polarized with a signal provided by oscillator 51 on wire 16. Oscillator 51 applies alternating current with a predetermined voltage and frequency to probe 30. It has been determined through experiments that a 5V peak to peak signal at 4.92 kHz, is optimal for sensing variations of the impedance between electrodes 25 and 26. In operation, the impedance between electrodes 25 and 26, varies due to variations in conductivity of the liquid. Therefore, the signal received from oscillator 51 is modulated by probe 30 in accordance with the conductivity of the milk between electrodes 25 and 26.

One input of a differential amplifier 56 is connected to probe 30 on line 18, to receive the modulated signal, and the other input receives a fixed reference voltage ($V_{ref}$). Differential amplifier 56 compares the modulated signal with the reference voltage $V_{ref}$ and outputs a ion detection signal each time the modulated signal is higher than $V_{ref}$. A counter 58, connected to the output of the differential amplifier 56, counts during the period when the ion detection signal is present, and outputs a variable count ($V_{count}$) signal. Counter 58 measures the percentage "ON" time during which the modulated signal remains higher than $V_{ref}$ and increments the $V_{count}$ every 10 msec. $V_{ref}$ is selected to give a $V_{count}=0$ for milk with less than 200,000 cells/ml and it is assumed that in this case no sodium ions are detected by probe 30. Counter 58 is set to zero before detector 50 starts sampling.

Control unit 40 receives the $V_{count}$ signal and converts same to a SCC score to be displayed on display 60. Control unit 40 controls the operation of detector 50, compares the count from counter 58 with the sodium ion detection thresholds corresponding to each section $p_i-p_{i+1}$ of the graph of FIG. 1C, and provides a SCC score to display 60. As it will be later described in connection with FIGS. 6 and 7, control unit 40 also receives information from a milk weight detector 45 providing data regarding the milk composition. Control unit 40 has two modes of operation namely Milk Quality Mode, wherein SCC scores are displayed, and Milk Yield Mode, wherein milk yield parameters are displayed.

The animal's body can act as a big capacitor causing a difference of voltage between the farm ground and the ground of device 10. This difference may be between 1 to 3 volts, variable from farm to farm, and can cause electrode contamination. Optocouplers 53–55 are provided to isolate sensing circuit 50 from the power source. The galvanically isolation of the sodium ion detector 50 reduces the offset current and increases measurement accuracy.

A thermistor 42 is also embedded in a plastic support and located inside the flow cell 20, close to probe 30. Thermistor 42 is connected to control unit 40 through a wire 15, for constantly providing unit 40 with on-line measurements of the milk temperature. The temperature is updated once every second and rounded up to the nearest 0.5° C. when displayed. Temperature monitoring at milking is an important parameter for decision making in herd management because it allows one to detect animals which are infected or under stress, and to take appropriate action.

Figure 3A:
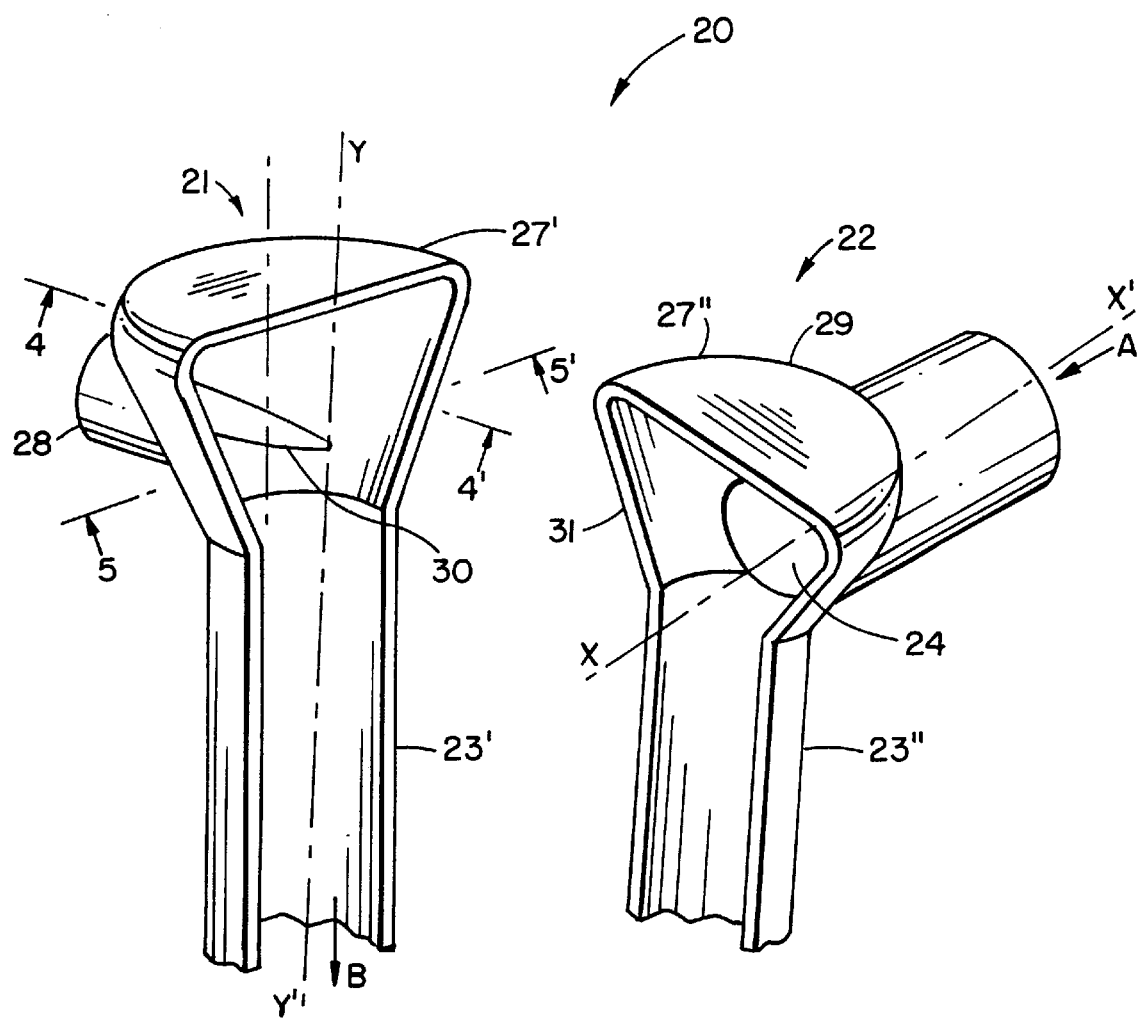
FIG. 3A is an exploded view of the flow cell of the present invention.

FIG. 3A is an exploded view of the flow cell 20, showing a left half 21 and a right half 22. It is to be understood that left half 21 and right half 22 are defined relative to the view of FIG. 3A. The position of the flow cell during sampling is irrelevant. When the left and the right halves are assembled, portion 27' of the left half 21 and portion 27" of the right half 22 form a frustroconical flow chamber 27 shown in FIG. 4 in further detail. Chamber 27 is defined by a large base wall 29, a lateral wall 31, and a small base forming an outlet 23. An inlet 24 is provided in the right half 22 for receiving the milk along an axis X–X', as indicated by arrow A. Probe 30 is placed inside chamber 27 on the opposite side of lateral wall 31 with respect to inlet 24. Portion 23' of the left half 21 and portion 23" of the right half 22 form, when assembled, the cylindrical outlet 23 defining axis Y–Y'. Milk is discharged from flow cell 20 through outlet 23, as indicated by arrow B.

Figure 3B:
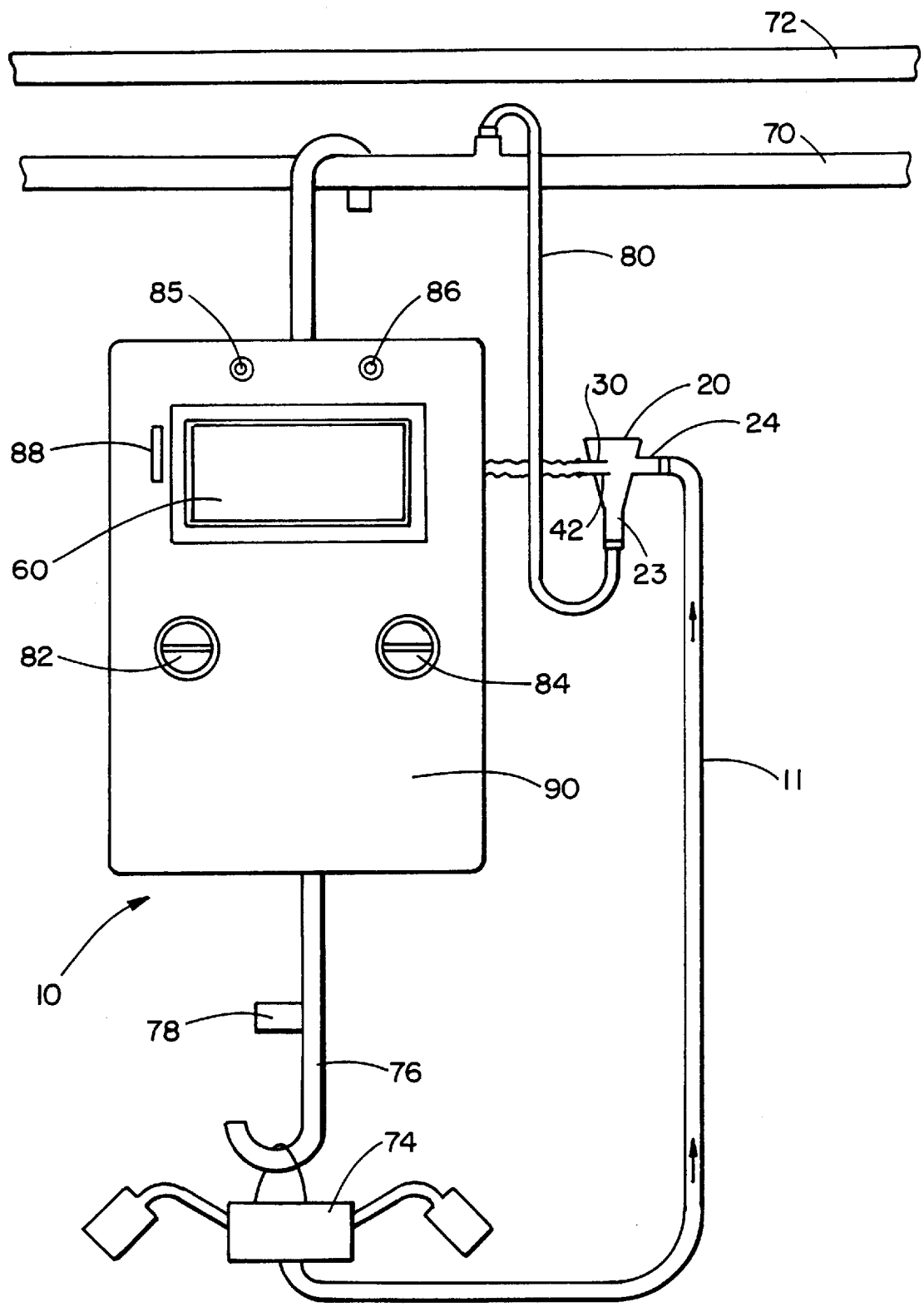
FIG. 3B is a schematic diagram of the analyser with the flow cell connected to a milking line.

FIG. 3B shows device 10 and flow cell 20 connected to the milk circuit. In general, the milk pipeline 70 travels along the milking stall in parallel to the vacuum line 72. Modern stalls are also provided with a 24 volt AC (not shown) for supplying power to suction teats engaging cups 74. Engaging cups 74 are attached to the pipeline 70 with a hook 76 or the like, provided with a handle 78 for moving cups 74 in and out of the milking position. Hook 76 also sup height for ease of reading.

When device 10 of the present invention is not used, engaging cups 74 are connected to pipeline 70 by a milking hose 11. When analyser 10 is used, flow cell 20 is inserted between milking hose 11 and pipeline 70 by connecting milking hose 11 to inlet tube 24 and a pipeline insert hose 80 is provided between outlet 23 and pipeline 70. Preferably, insert hose 80 is permanently attached to outlet 23. The inner diameter of the tubes 24 and 23 is a standard ⅝ inch, while the outer diameter is ⅞ inch, to fit the standard milk hose diameter. The flow cell 20 is preferably made of plastic by injection moulding. Flow cell 20 samples all quarters through milking hose 11.

Flow chamber 27 has an interior shape with improved flow dynamics, specially designed for accurate sampling. There are no milk flow obstructions which provides for a continuous flow inside flow cell 20. The interior shape of flow chamber 27 also provides for a constant number of droplets per volume of milk, regardless of the rate of flow. This uniform distribution of the milk droplets inside flow chamber 27, with no decrease in vacuum during milking, provides for accurate measurements and a one-time sampling of the milk, as it enters the flow cell 20. The shape of chamber 27 is also selected to minimize impurities and milk fat build-up around electrodes 25 and 26, by this minimizing the offset current.

Figure 4:
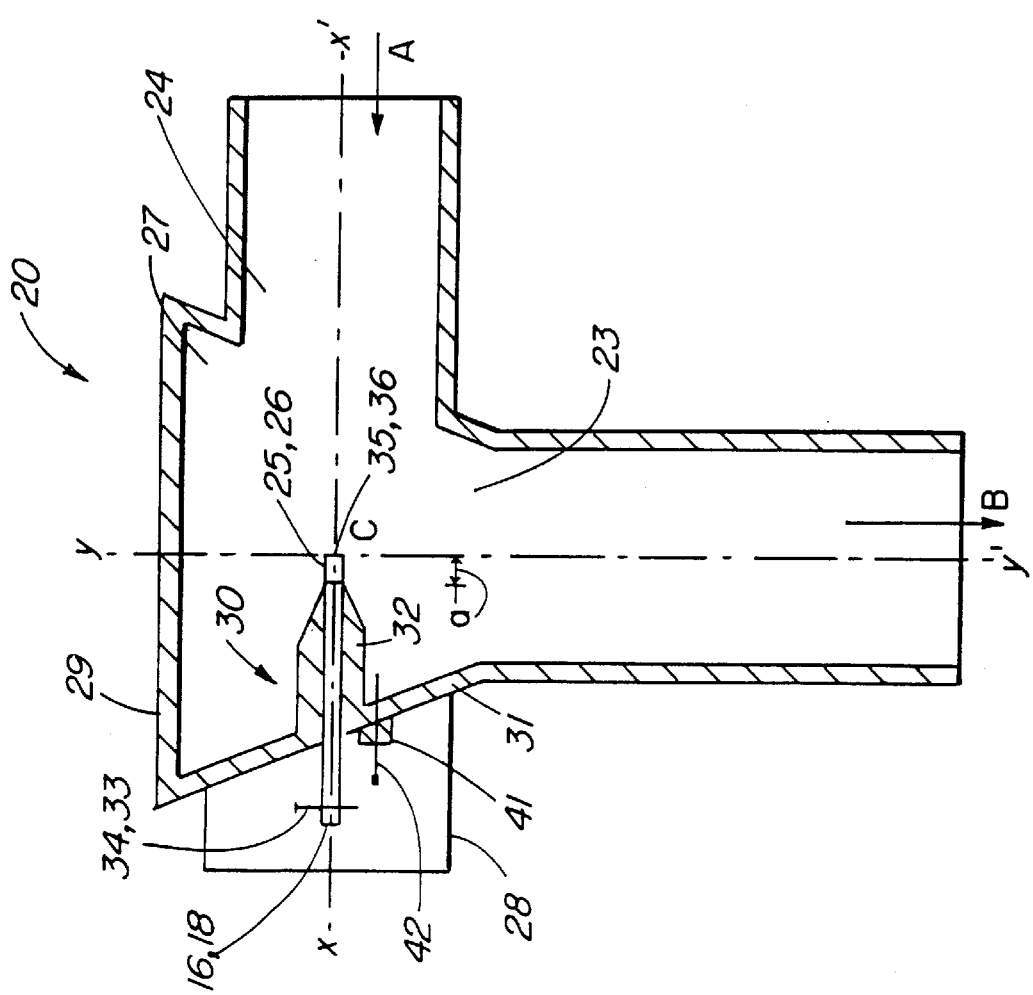
FIG. 4 is a longitudinal sectional view of the flow cell of FIG. 3A along lines 4–4' of FIG. 3A.

FIG. 4 is a longitudinal sectional view along lines 4–4' of FIG. 3A showing probe 30 inside flow chamber 27. The axes of inlet 24 and outlet 23 are perpendicular on one another, defining an intersection point C in the centre of the flow chamber 27. Probe 30 protrudes inside chamber 27 through the lateral wall 31 in an area diametrically opposed to inlet tube 24. Probe 30 comprises a plastic support 32 unitary with wall 31 of flow cell 20. It is important that electrodes 25 and 26, have a definite surface exposed for contact with milk. Tips 35, 36 of electrodes 25 and 26, are protruding through plastic bed 32 inside flow chamber 27 with a length "a" of approximately 1/20 of an inch. Tips 35, 36, better shown in FIG. 5, have flat, co-planar ends exposed to the flow of milk. Preferably, electrodes 25 and 26, contact the milk in a zone adjacent to point C, which is considered the zone of optimal sensing, because in this area the swirl of the milk is designed to create a virtually foam-free zone around electrodes 25 and 26, and the accuracy of the measurements is improved.

The other ends of electrodes 25 and 26 extend through plastic support 32 outwardly from flow chamber 27 and are provided with clamps 33, 34, for connecting to wires 16 and 18, respectively.

Figure 5:
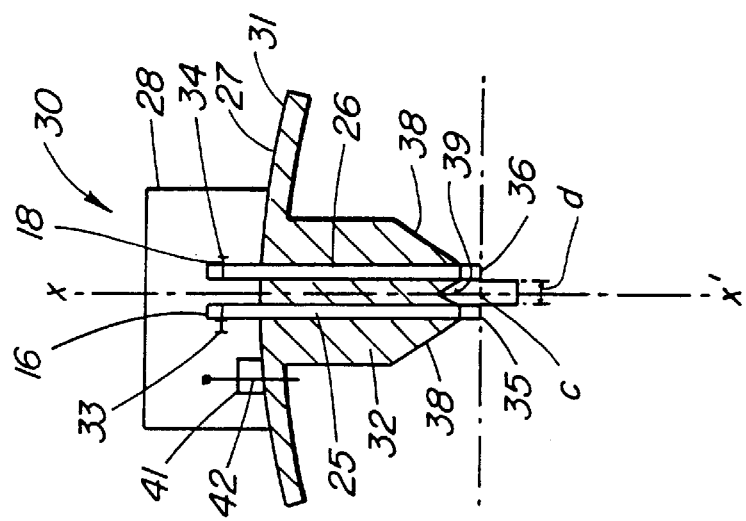
FIG. 5 is a transverse sectional view of the flow cell along lines 5–5' of FIG. 3A.

Thermistor 42 is located close to electrodes 25 and 26, as shown in both FIGS. 4 and 5. A plastic cover 28 is provided at the exterior of flow chamber 27 for protecting the electrical connections.

FIG. 5 is a transverse sectional view along lines 5–5' of FIG. 3A. Electrodes 25 and 26 are symmetrically positioned with respect to axis X–X' at a distance "d" from each other. A V-shaped portion 39 is formed between electrodes 25 and 26. Distance "d" is chosen as small as permitted by moulding strengths and cleaning factors. A length of approximately 1/25 of an inch is considered large enough to avoid the formation of deposits between electrodes and adequate for cleaning the flow cell after sampling. A suitable material for electrodes 25 and 26, may be a 1/16 of an inch, 304 stainless steel.

In operation, the analyser continuously displays data according to the SCC which is used as the international standard, as discussed before. The analyser of the present invention can also display the quantity of milk, butter fat percentage, protein percentage, milking time and the end-of-milking.

Milk Quality Mode

Figure 6:
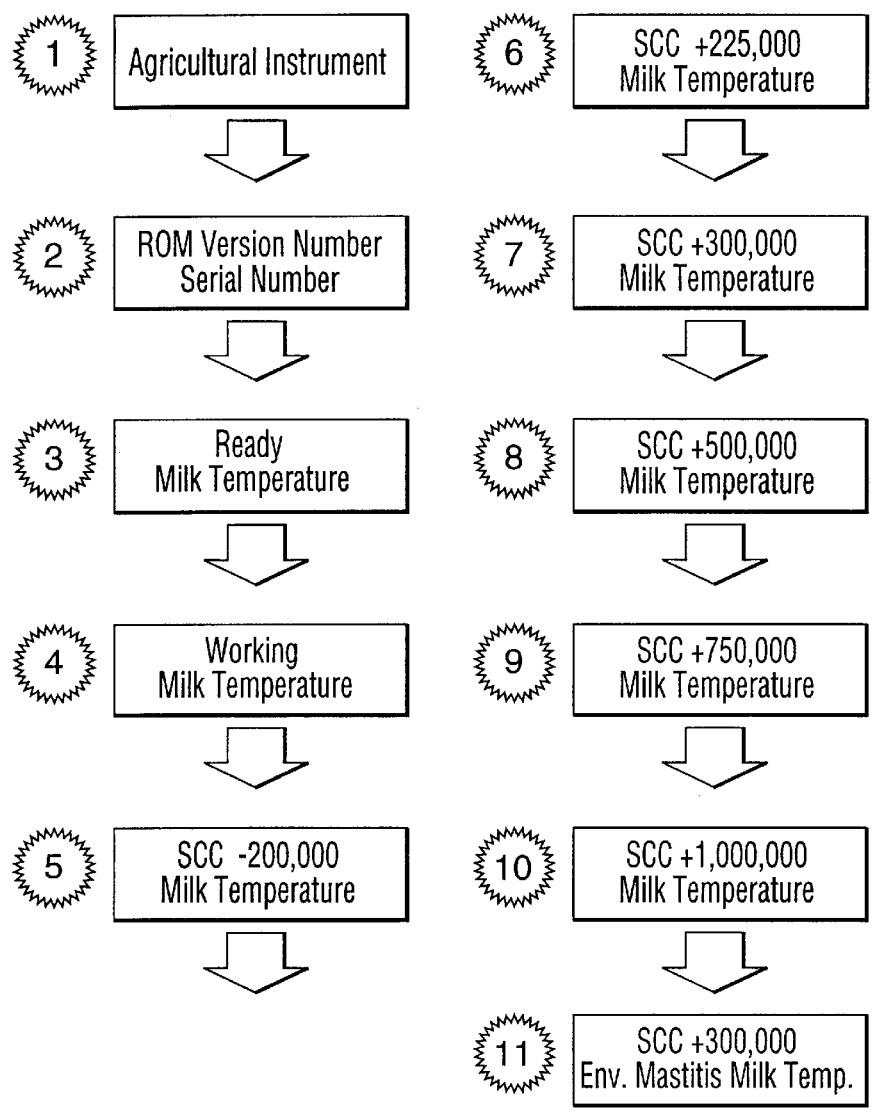
FIG. 6 is a pictorial view of the sequences displayed by the analyser in the Milk Quality mode of operation.

Milk Quality mode displays the somatic cell count and milk temperature. After powering up, analyser 10 sequentially shows the information in displays 1, 2, and 3, as shown in FIG. 6. After milk starts flowing, display 4 shows a rotating dial on the right upper corner of display 60 indicating that device 10 is operational, and milk temperature is displayed.

At the end of milking, the analyser indicates one of the displays 5 to 11, corresponding to the seven SCC scores. If the reading is greater than 500,000 cells/ml, lamps 85 and 86 on the analyser 10 will flash indicating a high somatic cell count.

Milk Yield Mode and Milk Quality Mode

Figure 7:
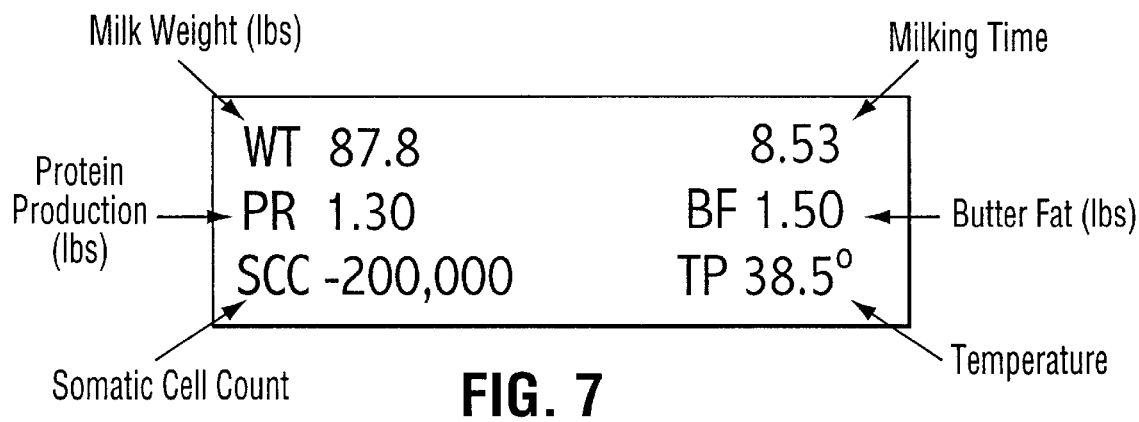
FIG. 7 is a pictorial view of a sequence displayed by the analyser when setup for both Milk Quality and Milk Yield modes of operation.

In the Milk Yield mode the milk weight, the milking time, the protein and the fat content are displayed in addition to the SCC and the milk temperature. The constant volume of flow through cell 20 multiplied by the milking time provides the milk weight. Analyser 10 can be setup for Milk Quality mode only, for Milk Yield mode only, or for both modes, as shown in FIG. 7.

Analyser 10 is shown at a much larger scale on FIG. 3B, to better illustrate the controls and the display. The somatic cell analyser 10 of the present invention is in fact a compact 145×105 cm box weighing half a kilogram. The LCD display 60 and red lamps 85, 86 are mounted inside the box under a transparent front face 90. A jumper switch 88, a reset button 84 and a reading button 82 are also disposed on the front face 90. The analyser 10 is fixed on hook 76 at a desired height.

Jumper switch 88 is used to switch modes by introducing new and modifying some existing operational amplifier parameters through software. This new circuitry is biased to the percentage of components in milk. This bias causes a maximum difference in count rate of 1.5%. The higher component level milk has a different viscosity causing a given amount of milk will act on probe 30 slightly longer. This causes a higher count per unit of milk.

Normal fat ranges are from about 3.6% to about 5.0%. Normal protein ranges are from about 2.9% to about 4.0%. Control unit 40 defaults the values to an average value 4.2% for fat, and 3.4% for protein. Given that fat and protein always move in proportion and that the outside values are close and that the circuitry is biased to milk components, device 45 can calculate a value in weight for fat and protein. This averaging technique provides an accuracy level of 0.05% in weight and consequently, makes device 10 also useful for feed management and nutrition requirement data collection.

In use, the farmer has to reset the analyser before each milking by pressing simultaneously the reading button 82 and the reset button 84, and then starts milking. The analyser 10 will acknowledge the end-of-milking and the farmer has to press the reading button 82 for displaying the results. Jumper switch 88 can alternate the displayed results according to the Milk Quality mode or the Milk Yield mode. An alarm is set and lamps 85, 86, flash if the SCC is over +500,000 cells/ml. The alarm can be set for any value of the SCC, according to the user's needs.

Numerous modifications, variations, and adaptations may be made to the particular embodiments of the invention described above, without departing from the scope of the invention as defined in the appended claims.

I claim:

1. A somatic cell analyser for on-line somatic cell count (SCC), comprising:

a flow cell for receiving a sample of milk;

detection means for providing an indication of the number of sodium ions in said sample and generating an ion count signal whenever the number of somatic cells is higher than a reference assumed to indicate absence of somatic cells in said sample;

control means for receiving said ion count signal, comparing same with a plurality of quality thresholds corresponding to a plurality of quality categories, and classifying said sample in a quality category; and means for indicating a set of parameters characterizing said quality category.

2. A somatic cell analyser according to claim 1, wherein said detection means comprising:

means for generating an ac signal;

a probe with two electrodes placed in said flow cell for modulating said ac signal according to the number of sodium ions in said sample and providing a modulated signal;

a comparator for comparing said modulated signal with said reference to produce a ion detection signal; and a counter for converting said ion detection signal into said ion count signal.

3. A somatic cell analyser according to claim 2, wherein said probe comprises:

a first electrode with a first end for receiving said ac signal;

a second electrode with a first end for providing said modulated signal; and means for electrically insulating said electrodes from each other along their entire body length but a tip at a second end of said first and second electrodes.

4. A somatic cell analyser according to claim 1, further comprising temperature sensing means for providing a temperature measurement to said control means.

5. A somatic cell analyser according to claim 1, further comprising a milk weight detector for providing said control means with data on components of said sample.

6. A somatic cell analyser according to claim 1, further comprising means for galvanically isolating said detection means.

7. A somatic cell analyser according to claim 1, wherein said flow cell comprises:

a flow chamber for accommodating said probe;

an inlet for connection to a first hose to admit a constant flow of the sampled liquid into said flow chamber; and an outlet for connection to a second hose to discharge the sampled liquid from said flow chamber.

8. A somatic cell analyser according to claim 7, wherein said flow chamber is frustroconical in shape, comprising:

a large base comprised of a continuous wall;

a lateral wall provided with said inlet and with a first support for said probe placed opposed to said inlet; and a small base provided with said outlet.

9. A somatic cell analyser according to claim 7, wherein said flow chamber further comprises a second support for said temperature sensing means, said second support being placed close to said first support.

10. A somatic cell analyser according to claim 7, wherein the axes of said inlet and said outlet intersect in a centre of optimal sensing.

11. A somatic cell analyser according to claim 9, wherein said tips of said electrodes have flat, co-planar ends equally spaced apart relative to said centre of optimal sensing.

12. A somatic cell analyser according to claim 7, wherein said first support comprises:

a plastic body having a V-cut portion symmetrically defined between said tips for exposing a predetermined surface of said electrodes.

13. A somatic cell analyser according to claim 2, wherein said ac signal has 5 Volts at about 4.92 kHz.

14. A method for on-line measurement of somatic cell count (SCC) using a somatic cell analyser, comprising the steps of:

preparing a SCC-sodium ion count graph by measuring a multitude of milk samples under laboratory conditions;

modifying said graph to a step graph comprising a plurality of SCC thresholds, each SCC threshold corresponding to a range of sodium ion counts and defining a quality category of milk;

storing said step graph into a memory of said analyser;

inserting a flow cell in the flow of milk for receiving a sample of milk;

measuring a ion count signal representing the number of sodium ions in said sample;

converting said ion count signal into a real time SCC; and identifying the position of said real time SCC on said step graph for classifying the milk in one of said quality category.

15. A method as claimed in claim 13, wherein said step of inserting a flow cell comprises:

connecting said flow cell between a first hose feeding milk from a source and a second hose supplying milk to the milk pipeline.

16. A method as claimed in claim 13, wherein said step of measuring comprises:

positioning a probe of said somatic cell analyser into said flow cell;

applying an ac signal to said probe to obtain a modulated signal carrying information on the number of sodium ions in said sample;

generating a ion detection signal based on said modulated signal; and converting said ion detection signal into said ion count signal.

17. A method as claimed in claim 13, wherein said step of comparing comprises:

selecting said thresholds in accordance with international standards; and calibrating said somatic cell analyser to provide a SCC value corresponding to one of said plurality of SCC thresholds for a range of ion counts measured with said SCC analyser.

18. A method as claimed in claim 13, further comprising the step of positioning a thermistor in said flow cell for measuring the temperature of said sample.

19. A method as claimed in claim 13, further comprising:

declaring a milk source infected with infectious mastitis whenever said analyser indicates a SCC corresponding to infectious mastitis; and declaring a milk source infected with environmental mastitis whenever said analyser indicates a SCC corresponding to environmental mastitis.

20. A somatic cell analyser for determining somatic cell count (SCC) in milk comprising:

a flow cell for receiving a sample of milk;

a sodium ion detector for determining the number of sodium ions in said sample; said detector generating an ion count signal whenever the number of somatic cells determined is higher than a reference count of somatic cells;

a control unit for receiving said ion count signal from said detector and classifying said sample in a quality category; and a display unit for displaying data categorized by said control unit.

21. A somatic cell analyser according to claim 20, wherein said sodium ion detector comprises:

an oscillator for generating an ac signal;

a probe having two electrodes placed in said flow cell for modulating said ac signal according to the number of sodium ions in said sample and providing a modulated signal;

a comparator for comparing said modulated signal with said reference to produce an ion detection signal; and a counter for converting said ion detection signal into said ion count signal.

22. A somatic cell analyser according to claim 21, wherein said probe comprises:

a first electrode with a first end for receiving said ac signal;

a second electrode with a first end for providing said modulated signal; and a protective cover for electrically insulating said electrodes.

* * * * *

UNITED STATES PATENT AND TRADEMARK OFFICE
CERTIFICATE OF CORRECTION

PATENT NO.   : 6,307,362 B1
DATED        : October 23, 2001
INVENTOR(S)  : Steven L. Mangan It is certified that error appears in the above-identified patent and that said Letters Patent is hereby corrected as shown below:

Column 10,
Line 47, "claim 1" should be -- claim 2 --;
Line 61, "claim 7" should be -- claim 8 --;

Column 11,
Line 1, "claim 9" should be -- claim 10 --;
Line 4, "claim 7" should be -- claim 8 --;
Line 31, "claim 13" should be -- claim 14 --;
Line 36, "claim 13" should be -- claim 14 --;
Line 48, "claim 13" should be -- claim 14 --;

Column 12,
Line 5, "claim 13" should be -- claim 14 --; and
Line 8, "claim 13" should be -- claim 14 --.

Signed and Sealed this

Twenty-fifth Day of June, 2002

Attest:

Attesting Officer

JAMES E. ROGAN
*Director of the United States Patent and Trademark Office*